(12) United States Patent
Cermak et al.

(10) Patent No.: US 8,073,529 B2
(45) Date of Patent: Dec. 6, 2011

(54) NEEDLE GUIDE SYSTEM FOR USE WITH ULTRASOUND TRANSDUCERS TO EFFECT SHALLOW PATH NEEDLE ENTRY AND METHOD OF USE

(75) Inventors: Craig J. Cermak, Riverside, IA (US); Brent A. Cumberford, Iowa City, IA (US); Roger F. Wilson, Sarasota, FL (US); Willet F. Whitmore, III, Longboat Key, FL (US)

(73) Assignee: CIVCO Medical Instruments Co., Inc., Kalona, IA (US)

( * ) Notice: Subject to any disclaimer, the term of this patent is extended or adjusted under 35 U.S.C. 154(b) by 672 days.

(21) Appl. No.: 11/970,797

(22) Filed: Jan. 8, 2008

(65) Prior Publication Data
US 2009/0143684 A1 Jun. 4, 2009

Related U.S. Application Data

(60) Provisional application No. 61/005,316, filed on Dec. 4, 2007.

(51) Int. Cl.
*A61B 5/05* (2006.01)
(52) U.S. Cl. ......... 600/424; 600/407; 600/437; 600/464
(58) Field of Classification Search .................. 600/437, 600/407, 459, 464
See application file for complete search history.

(56) References Cited

U.S. PATENT DOCUMENTS

| | | | |
|---|---|---|---|
| 5,031,634 A * | 7/1991 | Simon | 600/567 |
| 5,052,396 A | 10/1991 | Wedel et al. | |
| 5,076,279 A | 12/1991 | Arenson et al. | |
| 5,623,931 A | 4/1997 | Wung et al. | |
| 5,758,650 A | 6/1998 | Miller et al. | |
| 5,941,889 A * | 8/1999 | Cermak | 606/130 |
| 6,200,274 B1 * | 3/2001 | McNeirney | 600/562 |
| 6,361,499 B1 * | 3/2002 | Bates et al. | 600/461 |
| 6,379,307 B1 | 4/2002 | Filly et al. | |
| 6,475,152 B1 | 11/2002 | Kelly, Jr. et al. | |
| 6,758,817 B1 | 7/2004 | Pruter et al. | |
| 7,087,024 B1 | 8/2006 | Pruter | |
| 2005/0059891 A1 | 3/2005 | Kosaku | |
| 2005/0143753 A1 * | 6/2005 | Whitmore et al. | 606/130 |

FOREIGN PATENT DOCUMENTS

| | | |
|---|---|---|
| EP | 1552792 A1 | 7/2005 |
| WO | 2006041901 A2 | 4/2006 |

OTHER PUBLICATIONS

International Search Report for PCT/US2008/085244 dated Mar. 13, 2009.

* cited by examiner

*Primary Examiner* — Tse Chen
*Assistant Examiner* — Joel F Brutus
(74) *Attorney, Agent, or Firm* — Caesar, Rivise, Bernstein, Cohen & Pokotilow, Ltd.

(57) ABSTRACT

An ultrasound needle guide system for use with an ultrasound transducer and method of use of the guide system to provide predictable trajectories for puncture devices at various depths. The needle guide system basically consists of a bracket and a needle guide. The bracket is arranged to be releasably secured to the ultrasound transducer. The transducer/bracket assembly is then placed into an isolating sterile cover. The needle guide is arranged to be readily attached, e.g., snap-fit, to the transducer/bracket with the cover interposed therebetween. The needle guide can be provided in various versions for differing puncture device sizes and various entry angles in relation to the transducer. In one embodiment the needle guide is arranged to establish plural predetermined entry angles.

14 Claims, 7 Drawing Sheets

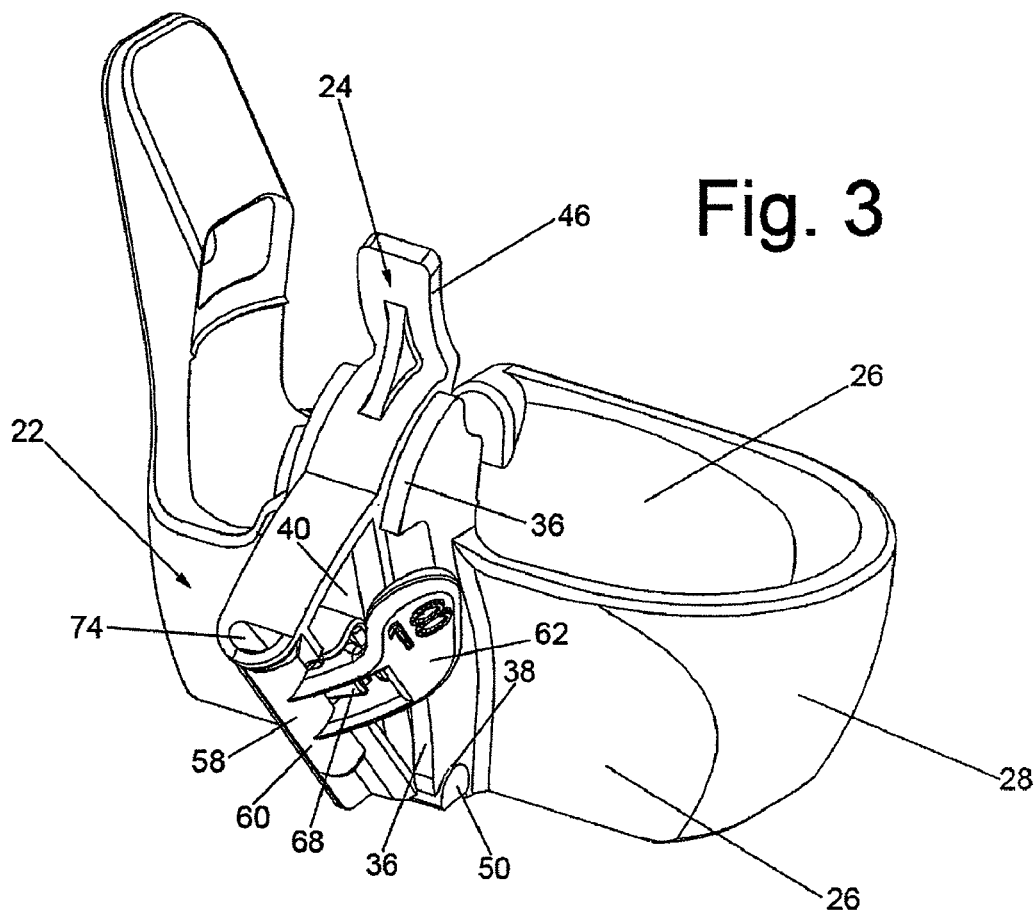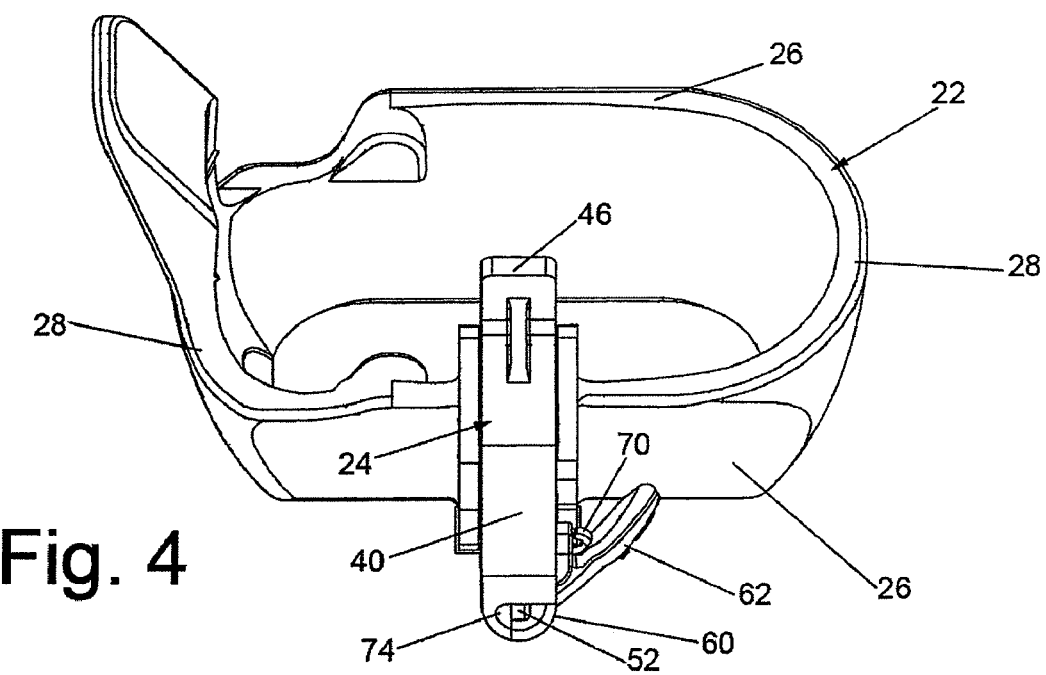

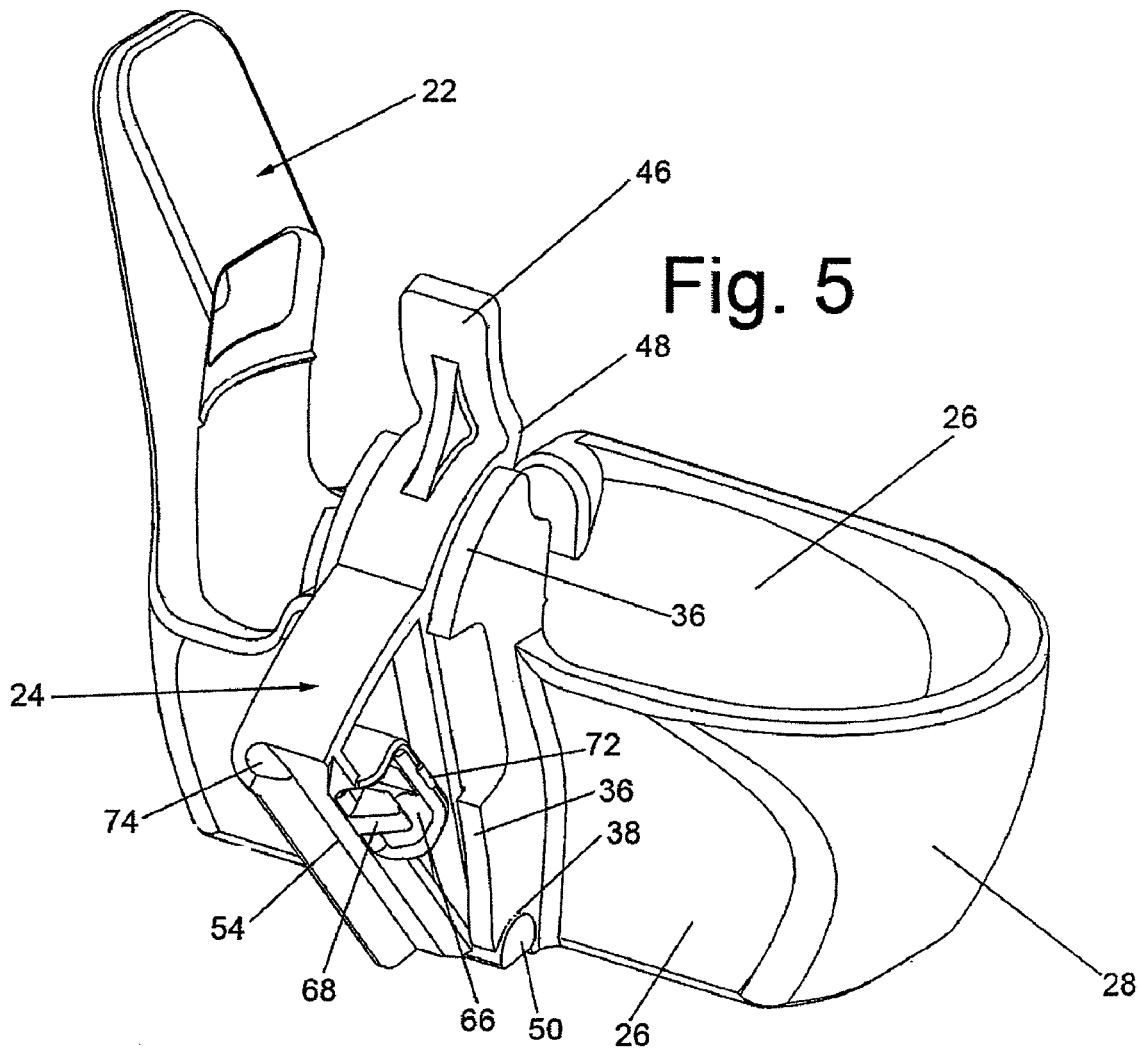
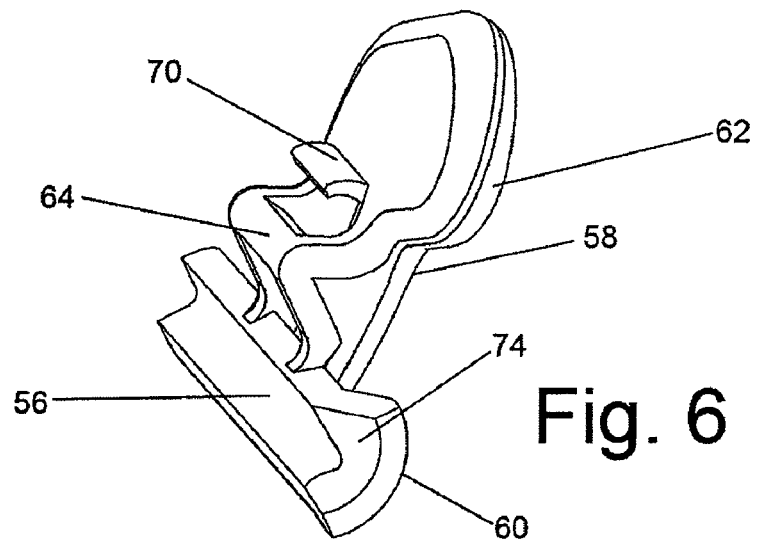

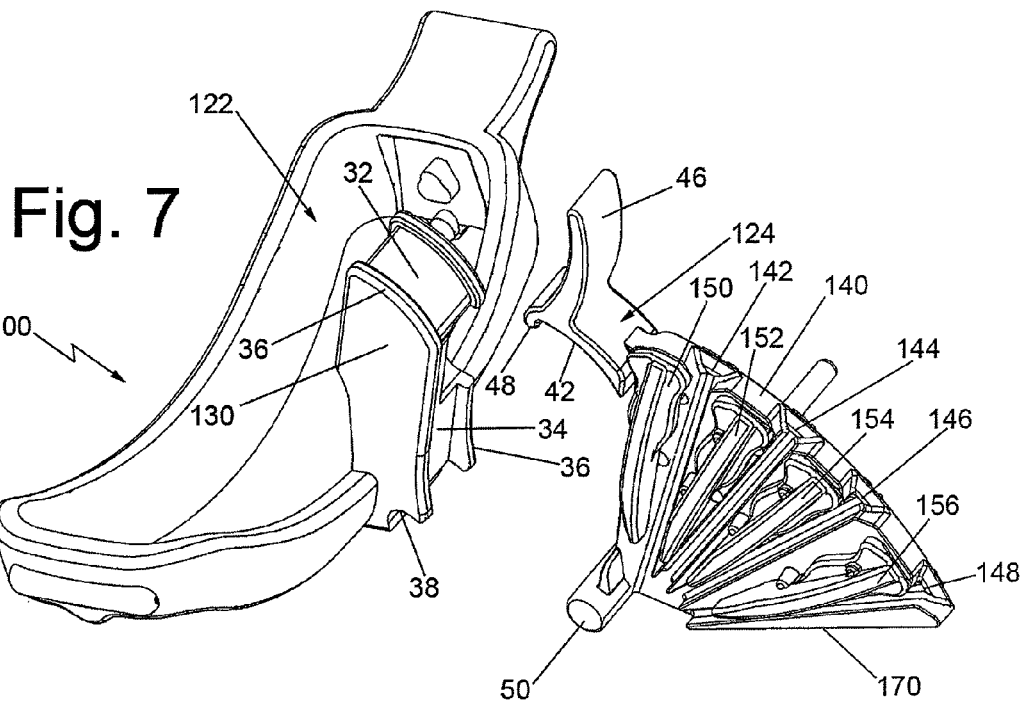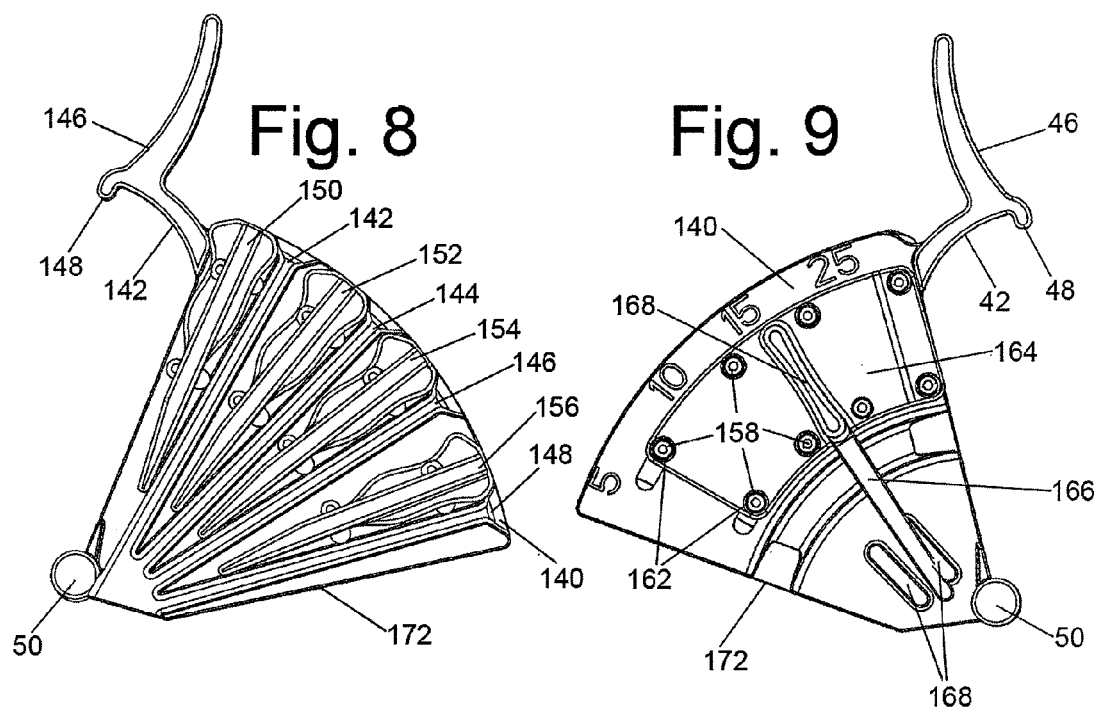

NEEDLE GUIDE SYSTEM FOR USE WITH ULTRASOUND TRANSDUCERS TO EFFECT SHALLOW PATH NEEDLE ENTRY AND METHOD OF USE

CROSS-REFERENCE TO RELATED APPLICATIONS PRIORITY

This application claims benefit of U.S. Provisional Patent Application No. 61/005,316, filed on Dec. 4, 2007, entitled NEEDLE GUIDE SYSTEM FOR USE WITH ULTRASOUND TRANSDUCERS TO EFFECT SHALLOW PATH NEEDLE ENTRY, the entirety of which is incorporated herein by reference.

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

BACKGROUND OF THE INVENTION

This invention relates generally to medical devices and methods of use and more particularly to needle guide devices and methods of use with ultrasound transducers.

It is a common medical practice to use a guide for releasable securement onto an ultrasound transducer to percutaneously guide a needle or some other puncture device to some desired location within the body of a patient. The patent literature includes various devices for such applications, such as those shown in U.S. Pat. Nos. 5,052,396 (Wedel et al.), 5,076,279 (Arenson et al.), 5,623,931 (Wung et al.), 5,758,650 (Miller et al.), 5,941,889 (Cermak), 6,379,307 (Filly et al.), and 7,087,024 (Pruter).

CIVCO Medical Instruments Co. Inc., the assignee of the subject invention through its related company CIVCO Medical Solutions, sells needle guide systems for use with ultrasonic transducers constructed in accordance with the above identified Filly et al. patent. Such systems consist of a custom reusable, non-sterile biopsy bracket or adaptor and a disposable, sterile snap-on needle guide. The bracket is sold under the trademark L17-5 multi-angle bracket and the needle guide is sold under the trademark Infiniti needle guide. The bracket is in the form of a ring-like member arranged to be releasably secured about a portion of the distal periphery of the ultrasound transducer. A flexible plastic, sterile isolating cover is then placed over the adaptor and the transducer to isolate those components from the patient and to provide a sterile field. The needle guide is then releasably secured, e.g., snap-fit to the adaptor, so that a portion of the cover is interposed between it and the adaptor. The needle guide is arranged to enable the physician or other health care provider to guide the needle or some other penetrating device to a desired location within the body of the patient. To that end, the needle guide basically comprises a pair of spaced apart plates. The needle or other puncture device is arranged to be placed between the plates and oriented at any desired angle to the central axis of the transducer so that the needle's tip can be inserted to any desired depth of penetration. The visualization of the positioning of the needle at the desired location is accomplished by the operation of the ultrasound transducer. The snap-fitting of the Infiniti needle guide to the L17-5 bracket is achieved by means of a pair of aligned grooves at the bottom of the bracket, which are arranged to receive respective projections or bosses located on the bottom of the needle guide to enable the upper portion of the needle guide to be pivoted toward an upper portion of the bracket. The upper portion of the needle guide is in the form of an under-cut arcuate recess. The upper portion of the bracket is in the form of an arcuate surface, which is arranged to mate with the undercut recess in the needle guide. A finger projects from the upper portion of the needle guide adjacent the undercut recess to enable the physician to grasp that finger during the pivoting of the needle guide toward the bracket so as to deform the undercut recess slightly, whereupon the curved surface of the bracket can snap-fit into the recess, thereby releasably securing the needle guide to the bracket with the isolating cover interposed therebetween.

While the aforementioned needle guide system of CIVCO Medical Solutions is suitable for its intended purposes, it still leaves something desired from the standpoint of needle or other puncture device guidance. In particular, the CIVCO Medical Solutions needle guide system does not provide a predetermined path for the needle or other puncture member to take, i.e., the needle or other puncture member can be oriented at any angle between the plates of the needle guide. Thus, a need exists for a needle or other puncture device guidance system for use with ultrasound transducers that facilitates precise positioning along at least one predetermined path. The subject invention addresses that need.

BRIEF SUMMARY OF THE INVENTION

In accordance with one aspect of this invention there is provided a puncture device guide system for use with an ultrasound transducer and a sterile cover to provide predictable trajectories for puncture devices at various depths. The puncture device guide system basically comprising a bracket and a puncture device guide. The bracket is arranged for releasable mounting on the ultrasound transducer, whereupon the sterile cover can be placed over the ultrasound transducer and the bracket mounted thereon. The puncture device guide is arranged to be readily attached, e.g., releasably snap-fit, to the bracket with the sterile cover interposed therebetween. The guide is constructed, e.g., it includes a base portion and a movable member which together form a passageway establishing a predetermined angled path for a receipt of a puncture device to penetrate into the body of a patient to a desired depth. The puncture guide is openable, e.g., the movable portion can be pivoted away from the base portion, to enable the ultrasound transducer with the needle guide system mounted thereon to be removed from the patient, leaving the puncture device in place penetrating into the body of the patient.

In accordance with one exemplary aspect of this invention the bracket includes a lower portion and the guide includes a lower portion. One of the lower portions of the bracket and the guide is in the form of a convex projection and the other of the lower portions of the bracket and the guide is in the form of a concave recess for mating receipt of the convex projection. This feature enables the guide to be pivoted about a pivot axis extending through the mating concave recess and convex projection in a first rotational direction to snap-fit the guide to the bracket.

In accordance with another exemplary aspect of this invention the movable member is biased to normally be in the pivotably closed position thereby establishing the predetermined angled path for a receipt of the puncture device.

In accordance with another exemplary aspect of this invention the system includes plural puncture device guides. Each of those plural guides is constructed to establish a different, respective predetermined angled path for a receipt of the puncture device.

In accordance with another exemplary aspect of this invention, the puncture device guide includes plural predetermined paths for receipt of a needle or other puncture device to establish plural preselected depths of penetration that can be achieved.

In accordance with another exemplary aspect of this invention the bracket is configured to be mounted on the ultrasound transducer so that the guide is located facing a transverse side of the ultrasonic transducer.

In accordance with another aspect of this invention there is provided a method for introducing a puncturing device into the body of a living being utilizing an ultrasound transducer to provide a predictable trajectory for the puncturing device at various depths. The method basically comprises providing a guide system comprising a bracket and a puncture device guide, releasably mounting the bracket on the ultrasound transducer, whereupon a sterile cover can be placed over the ultrasound transducer and the bracket mounted thereon. The method further entails releasably attaching the guide to the bracket with the sterile cover interposed therebetween to establish a predetermined angled path for a receipt of the puncturing device to penetrate into the body of a patient to a desired depth. The guide is openable to enable the ultrasound transducer and the needle guide system to be removed, leaving the puncture device in place penetrating into the body of the patient.

BRIEF DESCRIPTION OF SEVERAL VIEWS OF THE DRAWINGS

The invention will be described in conjunction with the following drawings in which like reference numerals designate like elements and wherein:

FIG. 3 is an isometric view of the adaptor shown in FIG. 1;

FIG. 4 is another isometric view of the adaptor shown in FIG. 1;

FIG. 5 is a slightly enlarged isometric view of the adaptor shown in FIG. 1, but with a portion of it, namely, the passageway forming clamp, removed;

FIG. 6 is a slightly enlarged isometric view of the passageway forming clamp of the adaptor shown in FIG. 1;

FIG. 7 is an FIG. 1 is an exploded isometric view of a second exemplary embodiment of a puncture device (e.g., needle) guide system making use of an adaptor and a needle guide which are constructed in accordance with this invention for use with a conventional ultrasound transducer;

FIG. 8 is a front plan view of the needle guide shown in FIG. 7;

FIG. 9 is a rear plan view of the needle guide shown in FIG. 7;

DETAILED DESCRIPTION OF THE PREFERRED EMBODIMENTS OF THE INVENTION

Figure 1:
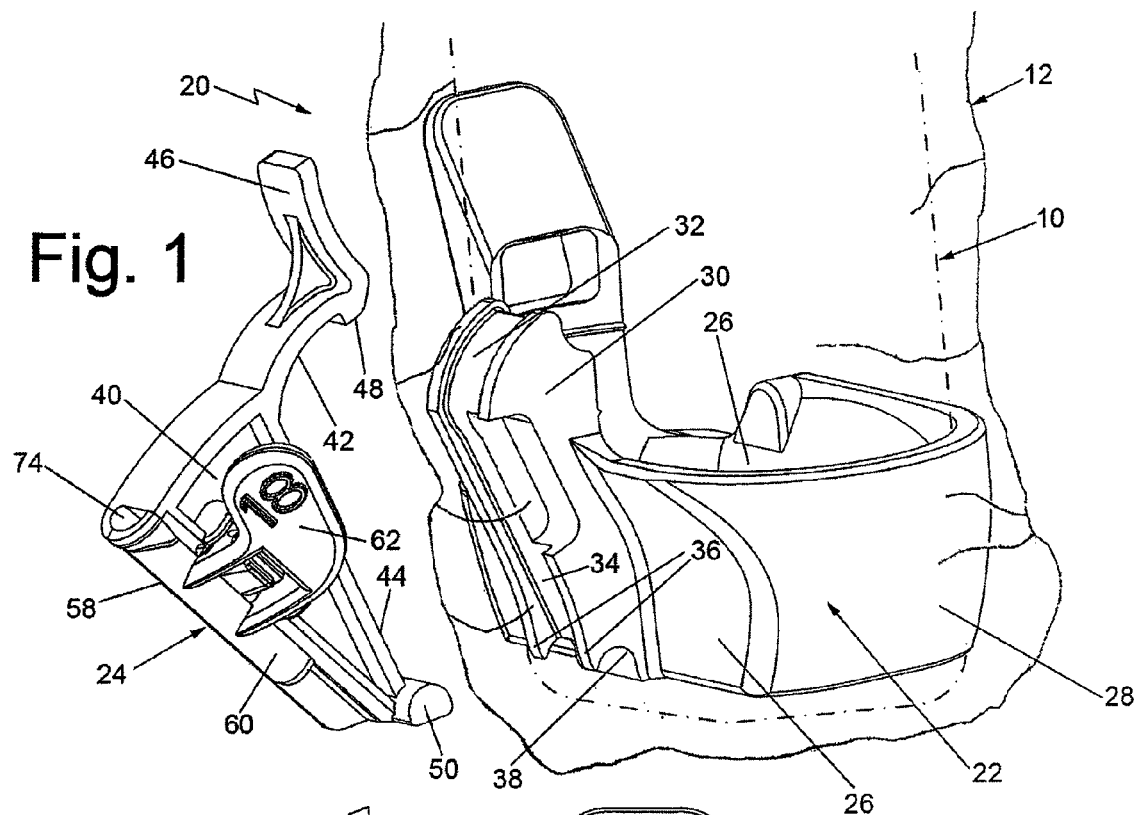
FIG. 1 is an exploded isometric view of one exemplary embodiment of a puncture device (e.g., needle) guide system making use of an adaptor and a needle guide which are constructed in accordance with this invention for use with a conventional ultrasound transducer and a sterile cover.

Referring now to the drawing wherein like reference numbers refer to like parts there is shown at 20 in FIG. 1 one exemplary embodiment of a puncture device guidance system for use with an ultrasound transducer constructed in accordance with this invention. The ultrasound transducer 10 is shown by the phantom lines in FIG. 1. Before describing the details of the system 20 a brief description of the ultrasound transducer 10 is in order. To that end, the ultrasound transducer 10 which is shown by the phantom lines is typical of the construction of conventional medical applications and typically has a central axis which is perpendicular to its distal end or patient engaging face. The cross section of the distal end is of a generally rounded rectangular or ovoid shape having a longer or major longitudinal axis and a shorter or minor transverse axis. Placement of a puncture device is typically accomplished by means of some needle guide mounted on one of the longitudinally extending sides of the transducer or on one of the transversely extending sides. In either case the needle or some other puncture device is arranged to brought in at an angle intersecting the transducer's central axis so that the tip of the needle or other puncture device is at a desired depth within the ultrasound transducer's imaging plane. Thus, the ultrasound transducer can provide an image of the field as the needle or puncture device is positioned in the imaging plane.

Figure 11:
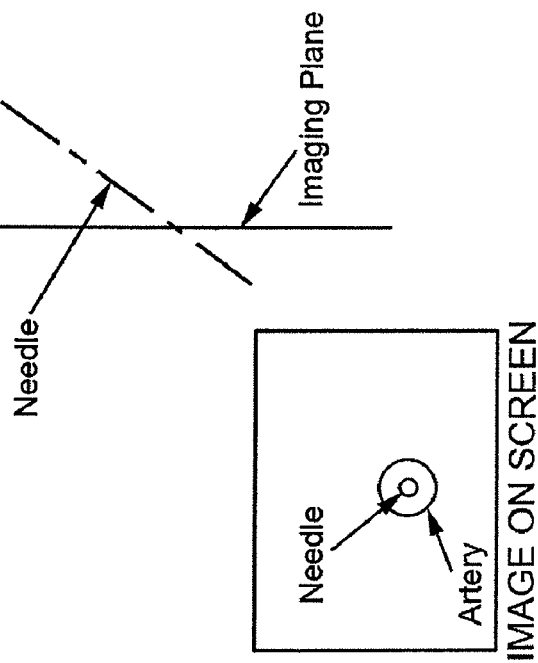
FIG. 11 is an illustration of an ultrasound transducer making use of a transversely mounted needle guide showing an exemplary image of the needle being inserted into an artery.

In FIG. 11 the ultrasound transducer 10 is illustrated showing a needle guide, like that of the subject invention, mounted "transversely" on the transducer. By "transversely" mounted it is meant that the needle guide is mounted so that the path that the needle takes with respect to the imaging plane intersects the imaging plane, thereby providing a cross section of the needle and the anatomic structure of the patient in which the needle is located, e.g., within an artery. The subject invention, is particularly suited for transverse mounting on the ultrasound transducer, but can also be arranged for longitudinal mounting. A longitudinally mounted needle guide is shown in the illustration of FIG. 11. As can be seen therein, with such an arrangement the angled path that the needle takes is in the imaging plane of the transducer.

The puncture device guidance system 20 basically comprises a bracket or adaptor 22 and a needle guide 24. The adaptor 22 is an integral unit which is best seen in FIGS. 1, 3, 4 and 5 and basically comprises a ring-like member having a hollow interior space shaped to accommodate the distal end portion of the transducer 10. The adaptor can be fabricated of any suitable material, e.g., molded of any suitable plastic. The ring-like portion of the adaptor is made up of an opposed pair of longitudinally extending side walls 26 and an opposed pair of transversely extending end walls 28, all of which are conjoined to one another. Since there are numerous shaped ultrasound transducers commercially available the shape of the inner surfaces of the side walls and end walls forming the ring-like portion of the adaptor will be configured to accommodate the particular transducer to which it is to be mounted. The adaptor is arranged to be releasably secured to the transducer via either frictional engagement or mechanical means, e.g., mating components of the transducer and adaptor. In either case the adaptor 22 is a reusable member that is mounted on the transducer 10. Then a conventional, flexible sterile cover 12, like shown in FIG. 1, is placed over the transducer on which the bracket is mounted.

The needle guide 24 is a sterile, preferably disposable member, which is arranged to be readily mounted on the adaptor 22 with the flexible, sterile cover 12 interposed therebetween, so that the needle guide is resistant to accidental disconnection, but can be readily removed (dismounted) when desired. In accordance with a preferred aspect of this invention the needle guide 24 is arranged to be connected to (mounted on) the adaptor 22 by means of a snap-fit connection. That connection will now be described. To that end, as can be seen in FIGS. 1-5 one of the longitudinally extending side walls 26 of the adaptor 22 includes a projection 30 extending outward from the outer face of that side wall. A channel 32 is provided in the outer surface of the projection 30, with the top portion of the channel forming a convex surface 34 and with the lower portion of the channel being somewhat linear. A pair of flanges 36 extends along the sides of the channel 32. The lower end of each flange 36 is in the form of a semi-circular recess 38. Each of the recesses 38 is arranged to receive a respective boss, to be described later, of the needle guide 24 to pivotably snap-fit the guide member to the adaptor 22.

Figure 2:
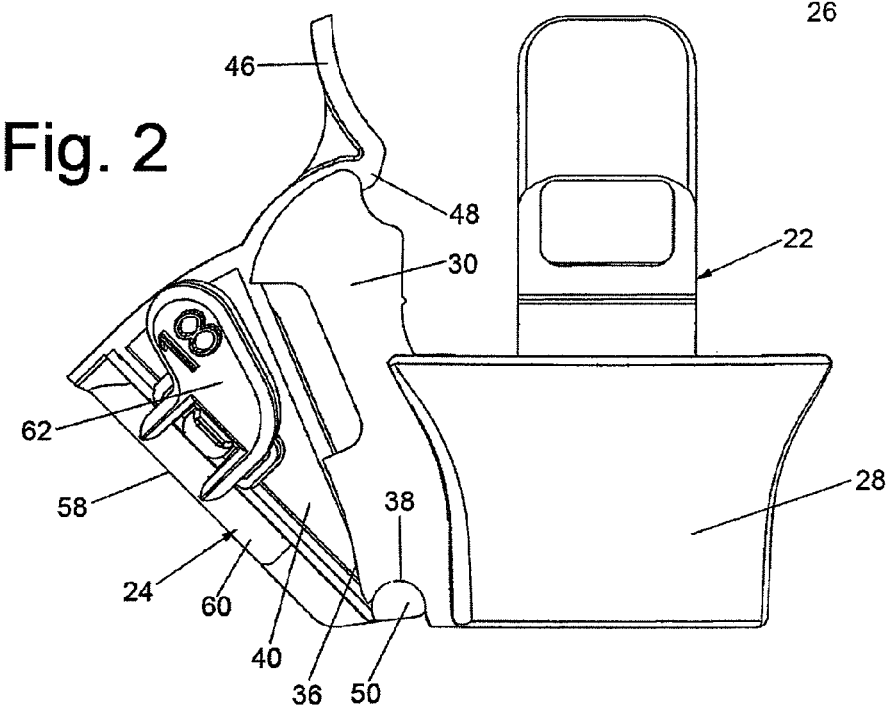
FIG. 2 is a front elevation view of the system shown in FIG. 1.

The needle guide 24 is best seen in FIGS. 1 and 2 and basically comprises a generally wedge shaped body 40 having an undercut recess 42 in the top portion of the front face of the body 40. The undercut recess is of a concave shape to mate with the convex surface 32 on the projection 30 of the adaptor 22. The remainder of the front face of the needle guide's wedge shaped body is in the form of a linear surface 44 whose width is just slightly less than the width of the channel 34 of the adaptor's projection 30 so that it can be received within the linear portion of that channel when the needle guide is mounted on the adaptor. The upper portion of the needle guide body 40 is in the form of a finger 46. A stop 48 projects downward from the finger 46 and forms the margin for the upper end of the undercut recess 42. Two semi-circular rods or bosses 50 project outward from the lower portion (the apex) of the needle guide body 40. The bosses 50 are axially aligned with each other.

The mounting of the needle guide 24 onto the adaptor 22 after the cover 12 has been placed over the transducer is accomplished as follows. The needle guide is juxtaposed so that its front face is disposed opposite to the channel 32 in the adaptor's projection 30, with the two bosses 50 of the needle guide being located within respective recesses 38 of the adaptor 22. The user then pivots the needle guide 24 towards the adaptor 22, using the finger 46 as a pull tab. This causes the stop 48 to slide along the upper convex surface 32 of the adaptor until it reaches the end of that surface, whereupon the finger 46 snaps downward, locking the stop 48 is place so that the convex surface 34 of the adaptor's projection 30 is resident within the undercut recess 42 of the guide member.

Figure 13:
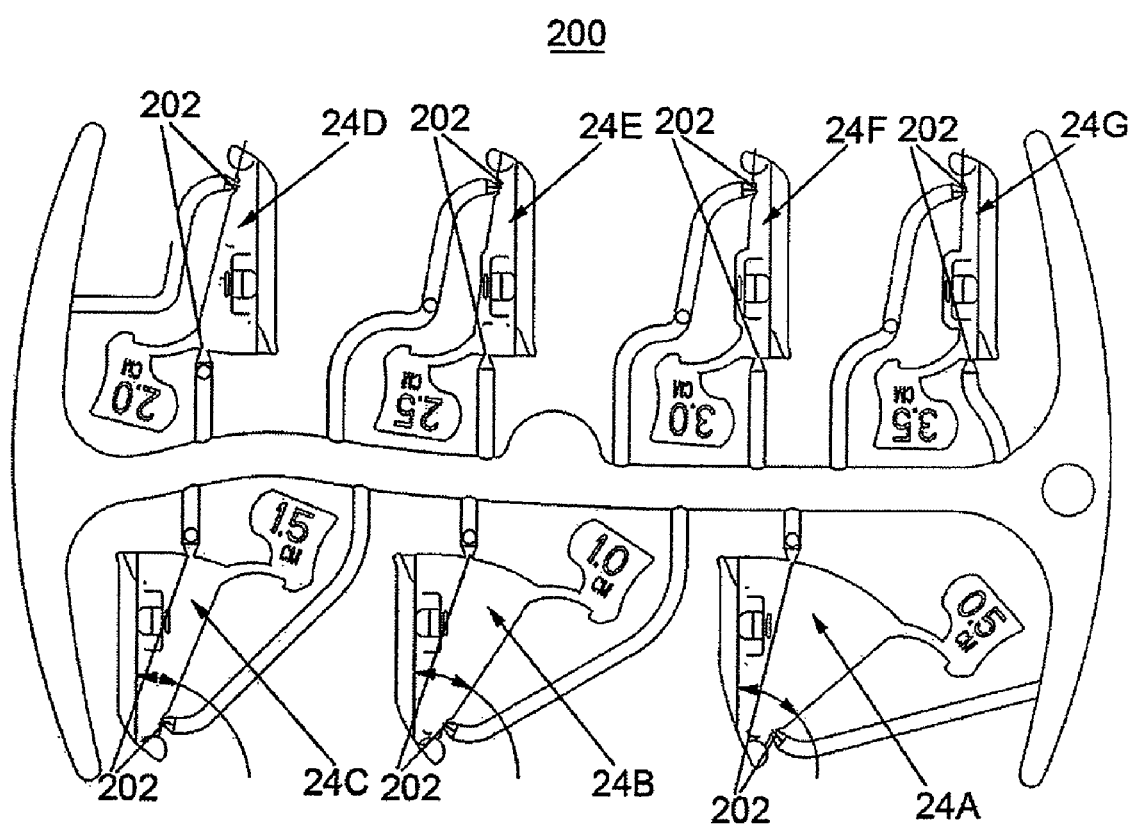
FIG. 13 is a top plan view of a kit having a plurality of needle guides for use with the adaptor shown in FIGS. 1-6 to establish penetration depths of 0.5 cm, 1.0 cm, 1.5 cm, 2.0 cm, 2.5 cm, 3.0 cm and 3.5 cm.

The needle guide 24 includes a passageway, to be described later, that establishes a predetermined path through which the needle may be extended to reach a desired depth of penetration. In particular, as will be described in considerable detail later the passageway in the needle guide is arranged to extend at an acute angle to the central axis of the transducer when it is mounted on the adaptor so that the intersection of the angled needle path with the central longitudinal axis of the transducer will be at the desired depth of penetration. That depth of penetration may be any desired depth. In accordance with one preferred embodiment of this invention plural needle guides may be provided, each establishing a different respective angular path, for use with a single adaptor to create different depths of penetration. For example, FIG. 13 shows a kit of plural needle guides 24A, 24B, 24C, 24D, 24E, 24F and 24G for producing a series of depths of penetration, e.g., 0.5 cm, 1.0 cm, 1.5 cm, 2.0 cm, 2.5 cm, 3.0 cm and 3.5 cm, respectively. The needle guides 24A, 24B, 24C, 24D, 24E, 24F and 24G are preferable molded as a unit 200 of any suitable plastic material and are provided in that form for use with an adaptor 22. When any particular needle guide is selected for use all that is required is to break it away from the other needle guides via the various breakaway joints 202. For example, if the physician wishes to have a needle penetration of 1.5 cm, e.g., to place the needle into an artery, the needle guide 24C would be selected and broken off from the remaining needle guides. Needle guide 24C is then be mounted on the adaptor in the manner as described above to establish a guide path taking the needle to a depth of penetration in the transducer's image plane of 1.5 cm.

The angular path established by each needle guide 24 is in the form of a linear passageway 52 (FIG. 4) which extends along the angled outside face of the wedge shaped body 40 of the needle guide. The passageway 52 is formed by the cooperation of an angularly extending linear groove 54 (FIG. 5) in the outside face of the guide member's wedge shaped body and a cooperating groove 56 (FIG. 6) in the inner surface of pivotable member 58. The pivotable member 58 is pivotably connected to the body 40 of the guide member by a hinge connection, to be described later. Suffice if for now to state that the pivotable member is biased, by means to be described shortly, so that it is normally in its closed position or orientation like shown in FIGS. 1-4, thereby establishing the predetermined angular path for the needle. The pivotable member is arranged to be moved, i.e., pivoted, to an open orientation to open the linear passageway 52 to enable the transducer and its attached needle guide system 20 to be removed from the patient, while leaving the needle in place in the patient.

As best seen in FIG. 6 the member 58 includes an elongated curved wall portion 60 (whose inner surface forms the groove 56) and a handle 62. A linear hinge pin 64 projects inward from the handle 62 and extends parallel to the groove 56. The hinge pin 64 is arranged to be pivotably received within a slot 66 in the wedge shaped body 40. The hinge pin is held in place within the slot by a retainer 68. A small, resilient arcuate shaped tab 70 is located on the inner surface of the handle 62 close to the hinge pin 64. The tab 70 projects outward from the member 58 and is arranged to abut a small ridge 72 (FIG. 5) on the body 40 of the guide member to apply biasing force to the member 58 to cause it to be in its normally closed orientation.

In order to facilitate the introduction of the needle into the passageway so that it can be guided along the passageway to its desired position within the body of the patient the proximal end of the passageway is flared at 74. The guide member 24 is arranged to be able to accommodate needles or other puncture devices of varying gauges. Thus, the guide member can be fabricated so that size of the passageway 52 is will accommodate needles of 18, 21 or 21 gauge. In fact, the passageway can be made to accommodate any size needle or other puncture device. In the exemplary embodiment shown in FIGS. 1-6 the needle guide is arranged for use with an 18 gauge needle. This is indicated by indicia bearing the number "18" appearing on the handle 62 of the needle guide.

The pivotable member 58 of the needle guide is arranged to be opened, i.e., pivoted away from the wedge shaped body 40, by pressing on the handle 62. This action causes the resilient tab 70 to bend or flex, whereupon the pivotable member 58 pivots outward from its closed orientation to an open orientation (not shown). In the open orientation the entire length of passageway 52 is accessible laterally. This enables the system 20 and the transducer 10 on which it is mounted to be removed from the patient leaving the needle in place in the patient, i.e., the combined transducer 10 and system 20 can be slid laterally off of the needle leaving the needle undisturbed.

As should be appreciated by those skilled in the art the needle guide attachment geometry as described above provides for very secure attachment without damaging the cover between the bracket and the needle guide. When the guide is attached to the bracket the finger (flexure) portion exerts pressure on the cylindrical bosses maintaining their position in the bracket's locating feature. When the device is used the routine manipulation of the transducer against the patient may exert pressure against the cylindrical bosses into the locating feature thus making the fit of the guide more secure. The flexure feature allows the guide to be attached and removed without friction between the bracket and the guide which is the most common cause of cover damage during guide attachment.

The secure fit of the as achieved by the subject is of considerable importance in transverse entry procedures, where the guide may extend beyond the bracket and be dislodged during routine manipulation of the transducer against the patient.

In FIGS. 7-10 there is shown another embodiment of a puncture device guide system 100 constructed in accordance with this invention. The system 100 is similar in many respects to system 20, except that its guide member 124 is arranged to provide plural predetermined paths, each establishing a different depth of penetration, whereas with the system 20 only a single depth of penetration can be effected by any given guide member 24. The system 100 basically comprises an adaptor or bracket 122 on which the guide member 124 is pivotably snap-fit. The adaptor 122 is similar in construction to the adaptor 22 in that it includes plural walls which conjoin to form a ring-like member for frictional or mechanical mounting on the distal end portion of the ultrasound transducer. The adaptor includes a projection 130 constructed similarly to projection 30 of the adaptor 22. Thus, the common structural element of the projection 130 will be given the same reference numbers as the projection 30 of the adaptor 22. Moreover, the details of the construction and operation of the projection 130 will not be reiterated in the interest of brevity. The guide member 124 is similar in construction to the guide member 24 insofar as its pivotable snap-fitting mounting on the adaptor 122 is concerned. Thus, the common structural elements of the means for snap connecting the guide member 124 to the adaptor 122 will be given the same reference numbers as the corresponding means for snap connecting the guide member 24 to the adaptor 22 and the description of the operation for snap connecting the guide member 124 to the adaptor 122 will be omitted in the interest of brevity.

The means of the guide member 124 for establishing the plural angled paths for the needle or other puncture devices will now be described. To that end as shown in FIG. 7, the guide member 124 includes a wedge shaped body 140 having plural elongated, linear grooves or slots 142, 144, 146 and 148. Since the slots 142, 144, 146 and 148 are open, the guide member 124 includes associated component in the form of pivotable cover plates 150, 152, 154 and 156, respectively, which are arranged to be pivoted to a closed position to seal the length of those slots, leaving only the distal and proximal ends of the slots open. Thus, when the cover plates are in their closed position, not shown, they cooperate with their associated slots to form the respective enclosed needle guiding passageways of the guide 124.

Figure 10:
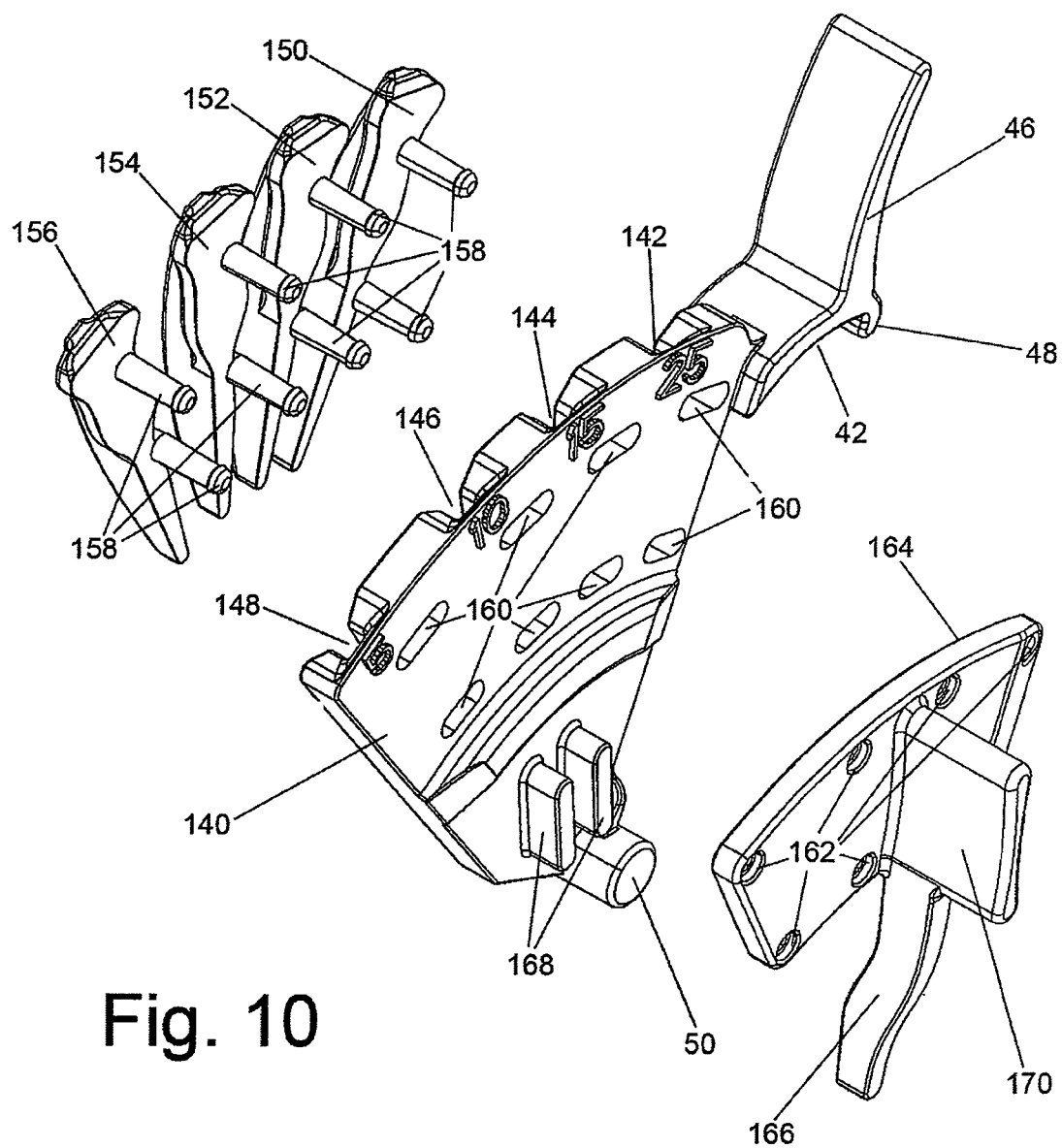
FIG. 10 is an exploded isometric view of the needle guide shown in FIG. 7.
Figure 12:
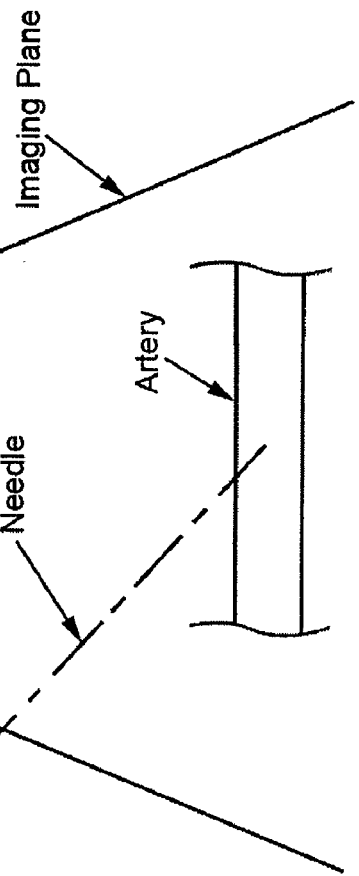
FIG. 12 is an illustration of an ultrasound transducer making use of a longitudinally mounted needle guide showing the needle being inserted into an artery.

As best seen in FIG. 10 each of the four cover plates 150, 152, 154 and 156 includes a pair of mounting pins 158 projecting perpendicularly from its rear surface. The pins 158 extend through arcuate slots 160 in the wedge shaped body 140 for fixed securement in respective apertures 162 in a pivot plate 164. The pivot plate is disposed on the opposite face of the guide member body 140 than the covers 150, 152, 154 and 156 so that the guide member body 140 is interposed between the cover plates and the pivot plate 164. The pivot plate includes an arm 166 which flexes as a spring when connected to the guide member body 140 between a pair of projecting stops 168. The pivot plate includes a handle 170 (FIGS. 9 and 10) to enable the user to readily pivot the pivot plate between the stops 168. The pivot plate is arranged to be pivoted outward, i.e., in a direction toward the outside face 172 of the guide member body 140 to cause the cover plates 150, 152, 154 and 156 secured to the pivot plate to also pivot in that direction, thereby causing them to enclose their associated slots. This action forms four, enclosed needle guide passageways for guiding a needle or other puncture device through it. In particular, the user can insert the needle or other puncture device into and through the desired passageway to percutaneously introduce the needle or other puncture device into the patient's body to the depth of penetration as established by the angularity of the selected passageway.

In the exemplary embodiment shown, the slot 142 extends at an acute to the front face of the wedge shaped body 140 to establish a depth of penetration of 2.5 cm, the slot 144 extends at an acute to the front face of the wedge shaped body 140 to establish a depth of penetration of 1.5 cm, the slot 146 extends at an acute to the front face of the wedge shaped body 140 to establish a depth of penetration of 1.0 cm and the slot 148 extends at an acute to the front face of the wedge shaped body 140 to establish a depth of penetration of 0.5 cm. As best seen in FIG. 8 the proximal end or entryway of each of the slots 142, 144, 146 and 148 is flared to facilitate the introduction of a needle or other puncture device therein.

In order to remove the system 100 and the transducer 10 on which it is mounted from the patient while leaving the needle or other puncture device in place undisturbed, all that is required is to pivot the pivot plate away from the outer face 170, thereby causing the associated pivot plates to pivot to the open position, i.e., a position laterally of their associated slots as shown in FIGS. 7 and 8. Once the slots are open the combined transducer 10 and system 100 can be slid laterally off of the needle leaving the needle undisturbed.

While the invention has been described in detail and with reference to specific embodiments thereof, it will be apparent to one skilled in the art that various changes and modifications can be made therein without departing from the spirit and scope thereof.

What is claimed is:

1. A puncture device guide system for use with an ultrasound transducer having a major longitudinal axis, a sterile cover and a puncture device for introducing the puncture device to various depths in the body of a patient, said puncture device guide system comprising a bracket and a kit of plural puncture device guides, said puncture device guides being arranged for forming discrete predetermined angled paths with respect to the major longitudinal axis of the transducer for guiding the puncture device to predetermined positions within the body of the patient, each of said discrete predetermined angled paths extending along a respective axis extending at a fixed and different angle to the major longitudinal axis of the transducer, said bracket being arranged for releasable mounting on the ultrasound transducer, whereupon the sterile cover can be placed over the ultrasound transducer and said bracket, each of said puncture device guides being arranged to be readily pivotably attached to said bracket with the sterile cover interposed therebetween to thereby establish a respective one of said discrete predetermined angled paths for a receipt of the puncture device to penetrate into the body of the patient to a different desired depth, each of said puncture device guides comprising a base member and a movable member, said movable member being pivotably connected to said base member about a pivot axis parallel to said predetermined angled path between a pivotably closed position and a pivotably open position and vice versa, whereupon when said movable member is in said pivotably closed position it forms a passageway between it and said base member, said passageway establishing said predetermined angled path for receipt of the puncture device, said moveable member when in said pivotably open position enabling the ultrasound transducer and the puncture device guide system on which it is mounted to be removed, leaving the puncture device in place penetrating into the body of the patient.

2. The puncture device guide system of claim 1 wherein each of said puncture device guides is arranged to be releasably snap-fit to said bracket with the cover interposed therebetween.

3. The puncture device guide system of claim 2 wherein said bracket includes a lower portion and each of said puncture device guides includes a lower portion, one of said lower portions of said bracket and each of said puncture device guides being in the form of a convex projection and the other of said lower portions of said bracket and each of said puncture device guides being in the form of a concave recess for mating receipt of said convex projection, whereupon each of said puncture device guides can be pivoted about a pivot axis extending through the mating concave recess and convex projection in a first rotational direction to effect the snap-fitting of each of said puncture device guides to said bracket.

4. The puncture device guide system of claim 3 wherein said lower projection of said bracket forms said concave recess and said lower portion of each of said puncture device guides forms said convex projection.

5. The puncture device guide system of claim 4 wherein said bracket includes an upper portion in the form of a convex surface and each of said puncture device guides includes an upper portion in the form of a concave recess for mating, snap-fit receipt of said convex surface when each of said puncture device guides is pivoted about said pivot axis in said first rotational direction.

6. The puncture device guide system of claim 5 wherein the ultrasound transducer also has a longitudinal side extending along said major longitudinal axis and a transverse side extending along said minor longitudinal axis, and wherein said bracket is configured to be mounted on the ultrasound transducer so that each of said puncture device guides is located facing the transverse side of the ultrasound transducer.

7. The puncture device guide system of claim 1 wherein the ultrasound transducer has a major longitudinal axis, a minor transverse axis, a longitudinal side extending along said major longitudinal axis and a transverse side extending along said minor longitudinal axis, and wherein said bracket is configured to be mounted on the ultrasound transducer so that said each of said puncture device guides is located facing the transverse side of the ultrasound transducer.

8. The puncture device guide system of claim 1 wherein said movable member is biased to normally be in said pivotably closed position.

9. The puncture device guide system of claim 1 wherein one of said puncture device guides produces a depth of penetration of 0.5 cm, a second of said puncture device guides produces a depth of penetration of 1.0 cm, a third of said puncture device guides produces a depth of penetration of 1.5 cm, a fourth of said puncture device guides produces a depth of penetration of 2.0 cm, a fifth of said puncture device guides produces a depth of penetration of 2.5 cm, a sixth of said puncture device guides produces a depth of penetration of 3.0 cm, and a seventh of said puncture device guides produces a depth of penetration of 3.5 cm.

10. A puncture device guide system for use with an ultrasound transducer, a sterile cover and a puncture device to provide plural predetermined discrete angled paths for introducing the puncture device to various depths in the body of a patient, the ultrasound transducer having a major longitudinal axis, said puncture device guide system comprising a bracket and a puncture device guide, said bracket being arranged for releasable mounting on the ultrasound transducer, whereupon the sterile cover can be placed over the ultrasound transducer and said bracket mounted thereon, said puncture device guide being arranged to be readily attached to said bracket with the sterile cover interposed therebetween and comprising a base member and a movable member, said base member including plural slots, each of said slots being oriented at a different predetermined fixed angle, said moveable member being pivotably connected to said base member, whereupon when said moveable member is in a pivotably closed position it forms plural respective passageways between it and said slots of said base member, each of said passageways extending at a respective predetermined angle with respect to the major longitudinal axis of the ultrasound transducer and establishing a respective one of said plural predetermined discrete angled paths for a receipt of the puncture device, each of said passageways being arranged for a receipt of the puncture device therein so that the puncture device can be guided therethrough to penetrate into the body of the patient to a respective different desired depth, said movable member being pivotable to a pivotably open position to thereby open said slots to enable the ultrasound transducer and the puncture device guide system to be removed from the puncture device, leaving the puncture device in place penetrating into the body of the patient.

11. The puncture device guide system of claim 10 wherein said plural predetermined discrete, fixed angled paths produce respective depths of penetration of 0.5 cm, 1.0 cm, 1.5 cm, and 2.5 cm.

12. The puncture device guide system of claim 10 wherein said bracket includes a lower portion and said puncture device guide includes a lower portion, one of said lower portions of said bracket and said puncture device guide being in the form of a convex projection and the other of said lower portions of said bracket and said puncture device guide being in the form of an a concave recess for mating receipt of said convex projection, whereupon said puncture device guide can be pivoted about a pivot axis extending through the mating concave recess and convex projection in a first rotational direction to effect the snap-fitting of said puncture device guide to said bracket.

13. The puncture device guide system of claim 10 wherein said ultrasound transducer also has a minor transverse axis, a longitudinal side extending along said major longitudinal axis and a transverse side extending along said minor longitudinal axis, said bracket being mounted on said ultrasound transducer so that said puncture device guide is located facing said transverse side of said ultrasound transducer.

14. The puncture device guide system of claim 10 wherein said movable member is biased to normally be in said pivotably closed position.

\* \* \* \* \*